United States Patent [19]

Shanni

[11] Patent Number: 5,631,012
[45] Date of Patent: May 20, 1997

[54] COSMETIC PREPARATIONS FOR MOISTURIZING HUMAN SKIN CONTAINING SPECIFIC LIPIDS

[76] Inventor: David Shanni, 1310 Cushing Rd., Scotch Plains, N.J. 07076

[21] Appl. No.: 300,794

[22] Filed: Sep. 2, 1994

[51] Int. Cl.$^6$ ..................................................... A61K 7/00
[52] U.S. Cl. ........................... 424/401; 424/59; 424/70.1; 424/73; 514/844; 514/847; 514/944
[58] Field of Search .................................. 424/401, 484, 424/59, 60, 64, 70, 73, 70.1; 514/844–847, 887, 944

[56] References Cited

U.S. PATENT DOCUMENTS 4,997,649  3/1991  Papaconstantin .................... 424/195.1
5,215,759  6/1993  Mausner ................................ 424/489

*Primary Examiner*—Gollamudi S. Kishore
*Attorney, Agent, or Firm*—Walter Scott

[57] ABSTRACT

Moisturizing cosmetic compositions for topical skin applications with an active component comprising a lipid mixture having approximately 1 part of specific mixed saturated fats, 1 part of specific monounsaturated fats, 0.25 parts of specific polyunsaturated fats, 4 parts of specific phospholipids, 2 parts of glycolipids and trace quantities of waxes and aminolipids. The formulated topical cosmetic products containing the lipid mixture impart moisturizing skin effects totally safe and highly efficacious. The proportions of lipids approximate those of the vernix.

3 Claims, No Drawings

COSMETIC PREPARATIONS FOR MOISTURIZING HUMAN SKIN CONTAINING SPECIFIC LIPIDS

FIELD OF THE INVENTION

The present invention relates to cosmetic preparations for the moisturization of human skin and more particularly to cosmetic preparations using naturally occurring and/or synthetically produced vernix as the major active ingredient.

BACKGROUND OF THE INVENTION

The present invention relates to cosmetic product compositions exhibiting the ability to moisturize human skin and leave the skin feeling soft and supple for extended time periods. In particular, it relates to the use of naturally occurring and/or synthesized vernix lipid mixtures in the same proportionate mixture. The vernix composition is composed of a specific ratio of fats commonly known as saturated fats at about 1 part, fats commonly known as monounsaturated fats at about 1 part, fats commonly known as polyunsaturated fats at about 0.25 parts, fats commonly known as phosopholipids at about 4 parts, fats commonly known as glycolipids at about 2 parts and minor quantities of fats known as aminolipids and waxes.

The vernix (commonly known as vernix caseosa or vernix caevsa) is a cheesy deposit on the surface of a human or animal fetus derived from the stratum corneum, sebaceous secretion, and remnants of the epitrichium. This naturally occurring deposit is of a specific composition with extraordinary properties for keeping the fetus' skin soft and moist.

Heretofore, individual fatty compositions and/or types of lipids have been utilized in various compositions having some skin moisturizing property. However, various side effects such as irritation, sensitization, odor, greasy feeling, acne, comedogenicity, and allergic effects, have been experienced.

It is well recognized that the most important function of the human skin is to protect the body from adverse environmental factors which tend to dry and flake the skin. This barrier of skin derives some added protection from the complex lipid layer that covers the skin surface and extends over the surface of skin. The natural lipid layer slows down the absorption of foreign substances at least for short contact periods, and it confers to the skin water shedding properties.

Some alterations of the normal properties and functions of skin interfere with its barrier qualities. Exposure of the skin to low humidity such as that found in heated buildings in winter, various detergents, and soaps, industrial chemicals, solvents, wind, cold, heat and sun may at times damage the skin. Protection such as applying oils, petrolatum, various creams and lotions containing moisturizers prevent water loss from the skin's surface. However, apparent side effects may also occur affecting the skin's properties or functions in deeper skin layers.

It is further recognized that if the skin is damaged due to some external effect which causes dryness to occur it is unable to function as a protective barrier. The lipid film on the surface of the skin is of major importance in maintaining flexibility and in keeping the skin barrier integral for preventing dryness. Absence of the moisturizing lipids causes dehydration, resulting in chapping.

The lipid layer on the skin is composed of a hydrophilic mixture of free and esterified cholesterol, other sterols, fatty acids, waxes, fats and hydrocarbons. Cholesterol is hydrophilic, however its esters are hydrophobic. Therefore, the lipid film participates in a dual function. The hydrophobic deeper layers of the skin shed water while the hydrophilic outer layers retain water in an emulsified form to maintain the skin generally soft and supple.

The main characteristic of the skin's lipid layer is manifested in the intense interest focused in finding suitable materials to supplement its moisturizing ability. Lanolin has been suggested for this purpose, since the skin's surface lipids of all mammalian species were thought to be similar to that of humans. However, there are marked differences in composition between lanolin and the lipid layer on the surface of the human skin. Lanolin is composed of hydrophobic esters which oppose absorption of water whereas human skin lipids are hydrophobic and hydrophilic as well.

Moisture loss from the skin can be reduced by using water repellant films such as petrolatum but it can cause maceration by preventing even normal moisture loss from the skin. Various lanolin derivatives are used in order to obtain more hydrophilic effects than lanolin and obtain water-resistant films purported to be less occlusive than petrolatum. These products function as skin lubricants as well. However, lanolin has been reported to cause allergic reactions in a high number of individuals.

There is another classification of moisturizers which are water soluble and generally referred to as demulcents, which are glycerine, sorbitol and various other polyols. These substances hold water in close contact with the skin and thus supply water to the epidermis. These agents also supply a softening effect on the skin when applied at suitable concentration and in suitable vehicles.

There are fats and oils of vegetable and animal origin which are used in cosmetic formulations for their emollient, occlusive properties and moisturizing properties. However, problems such as stability of these products require use of additives or stabilizers which in turn have caused dermal problems resulting from the stabilizers used in the cosmetic formulation. Phospholipids have also been used in various creams and lotions as moisturizers. These lipids are complex fat substances found in living cells. Lecithin is an example of a typical phospholipid substance. The classical moisturizer has always been recognized as cold cream based upon oils in a cream form.

Many of the ingredients already discussed are used for their moisturizing properties. However, because the conservation of body moisture has been associated with beauty care, a host of specialized cosmetics has been created exclusively for this purpose. They may be known under various names such as hand and body lotions, day creams, facial moisture creams, nail moisturizers, complexion lotions, etc. Despite such apparent diversity, they all work in pretty much the same fashion. To understand the common features of these products (and all secondary moisturizers like cold creams), one must look at the clinical problems that justifies their use.

Dry skin affects most people at some point in their lives, particularly the older and light-skinned. Usually, it occurs on hands and legs and, to some extent, the face. Even though it is known that loss of the skin's moisture leads to flaking, chapping, or other irritation of body surfaces, no one knows precisely how to define the problem—not even dermatologists and cosmetologists.

The oily secretions of the sebaceous gland seem to help protect the skin from foreign substances. These secretions, in conjunction with sweat, form a smoothing film that supplies skin with luster, depth of color, and an evaporation barrier. The scalp, face and shoulders have abundant amounts of sebaceous glands. Other portions of the body have fewer glands and are more susceptible to drying out. Hands and legs are doubly vulnerable because they produce little oil and are frequently exposed to harsh weather and chemicals. Scientific studies seem to indicate that only two moisturizers cause significant long-term improvements. These are lanolin and petroleum jelly (petrolatum). For short-term relief from dry skin, such as that resulting from washing, exposure to drying conditions, almost any commercial product works.

It is apparent from consumer studies that moisturizing preparations do have limited value in helping dry skin among certain people at certain times. Older persons with diminishing secretions from their sebaceous glands may well want to use a product containing petroleum jelly or lanolin. the usefulness of moisturizers for the rest of the population, however, is doubtful. As in the case of cold creams, facial lotions can clog pores that eventually fester when such products are applied too frequently.

While it is not exactly clear how moisturizers work, dermatologists and cosmetologists do know that oil is the key to all lubricating, moisturizing, and softening products. Without oils, these preparations would be ineffective, even though oils have no ability to moisten skin. They do, however, somehow help the skin remoisturize itself.

The oils or emollients found in these products may be as commonplace as lard or peanut oil, a little more refined like mineral oil and petrolatum, or more complex laboratory discoveries such as dimethicone and synthetic spermaceti. Whatever the oil used in a lotion, it will, to some extent, mask the effects of dry skin by lubricating and smoothing the skin's inherently rough surface.

Petrolatum and lanolin head the list of effective emollients. Both of these substances are commonplace and relatively inexpensive. (Some people are allergic to lanolin.) However, the cosmetic industry has abandoned simplicity for elaborate formulations full of various ingredients. Some of these more sophisticated and expensive creams and lotions may have an attractive scent and feel less greasy than plain petroleum jelly. However, unless they contain this basic emollient or lanolin, they will probably prove to be ineffective in the long run.

Water is even more of a common denominator in moisturizing cosmetics than oils are. This water has nothing to do with moisturizing the skin, but rather with providing good consistency and spreadability of the product. Products containing water usually have humectants to prevent evaporation that would leave the cream too thick or hard. These water retainers help keep lotions usable over a long time, but they apparently do not attract needed moisture to dry skin. But some humectants do serve a useful function as emollients.

Preservatives are another type of ingredient required in many water-oil emulsions. Certain types of natural oils and water combine to form a favorable environment for the growth of microorganisms. Without preservatives, products contaminated with bacteria could possibly lead to infection of sensitive areas like abraded skin or the eyes. The more complex moisturizers contain a number of other substances that are totally unrelated to the effectiveness and preservation of the formulation. Among such are thickeners, which are added because some consumers associate rich, heavy creams with luxury and moisturizing power. There are also emulsifiers to hold the water and oils together.

Once again, it is important to mention the potential side effects of moisturizers for producing acne. But there are other hazards connected with these products that have not received as much public attention. Allergies are a case in point. Any cosmetic frequently applied to large areas of skin and composed of endless varieties of chemicals will inevitably cause trouble for at least some users—particularly when it is left on the skin, as most skin products are. The longer toxic chemicals remain on the skin, the greater the chance of their causing harm to the skin surface.

A number of common ingredients in skin creams that most frequently trigger allergies and cause skin irritation among consumers. However, many of these substances are not essential to a good moisturizing preparation. The inclusion of lanolin in moisturizers may pose a problem for consumers. This natural oil is an excellent long-term lubricant of the skin, but some people are allergic to it. Moisturizer containing safer, derivative compounds from lanolin, such as acetylated lanolin, may be used.

DESCRIPTION OF THE PRIOR ART

Many prior art patents disclose the use of lipids in combination with certain other ingredients which provide moisturizing skin preparations. For example, U.S. Pat. No. 3,957,971 discloses moisturizing compositions containing liposomes, each having a matrix of a ternary lipid mixture of lecithin, dicetyl phosphate, and a sterol. Also, included within the preparation is a humectant such as sodium pyroglutamate, in an aqueous medium.

U.S. Pat. No. 4,457,910 discloses cosmetic composition products wherein the major active ingredient is a non-ionic surfactant having a hydrophilic-lipophilic balance of 12 or less. Examples of these non-ionic surfactants are as follows: $C_6$ polyol fatty acids esters such as sorbitan fatty acid esters, polyoxyethylene sorbitol esters, polyoxyethylene alcohols, and polyoxyethylene sorbitan fatty acid esters, and mixed fatty acid ester blends.

U.S. Pat. No. 4,760,096 discloses skin moisturizing preparations containing such ingredients as lecithin, $C_{10}$–$C_{30}$ carboxylic acid sterol esters, and other ingredients like $C_6$–$C_{12}$ alkanoic triglycerides, such as caprylic or capric triglycerides.

None of the aforementioned prior art patents discloses or suggests the use of vernix as an active ingredient of vernix, as part of their product components.

Accordingly, it is an object of the present invention to provide various cosmetic component preparations for the moisturization of human skin.

Another object of the present invention is to provide a physiological active agent capable of improving skin softness, flexibility, plasticity, elasticity and moisturization.

Another object of the present invention is to provide such a skin moisturizing active agent which comprises the material vernix.

Another object of the present invention is to provide the vernix as a naturally occurring material from mammalian fetuses or as a synthetically produced entity from commercially manufactured chemical compounds.

Another object of the present invention is to provide a cosmetic preparation in combination with vernix and other component materials which produce hypoallergenic products.

Another object of the present invention is to provide a cosmetic preparation in combination with vernix and other component materials which will produce compositions that will not support the growth of bacteria.

Another object of the present invention is to provide a cosmetic preparation in combination with vernix and component materials which produce products that are biodegradable.

Another object of the present invention is to provide a cosmetic preparation in combination with vernix and component materials which produce products that have long lasting effects on the skin and results in longer effective treating times for any active ingredient which may be added.

It is still another object of the present invention to provide such topical cosmetic preparations in the form of moisturizing lotion, moisturizing skin cream, massage cream, body lotion, face cream, skin healing ointment, sun screen gel, suntan lotion, lip pomade, sun screen lip balm, hand lotion, foot cream, hair lotion, after shave moisturizer, moisturizing shampoo and the like.

A still further object of the present invention is to provide a method of treating dry and flaky skin conditions by topically applying the various cosmetic preparations as disclosed herein.

An even further object of this present invention is to provide such topical cosmetic preparations which really do improve from a physiological standpoint, the condition of dry and flaky skin such that the treated skin areas provides a smooth, silky, velvety, long lasting feel after treatment.

The formulations and methods by which the above objects may be accomplished are disclosed in the detailed description of the present invention which follows hereinafter.

SUMMARY OF THE INVENTION

In accordance with the present invention a novel and effective composition is provided for treatment of dry skin, acting as a moisturizer which functions as a protective barrier between the skin and the environment. Although the skin manufactures its own natural moisturizing oils they are removed by cleaning or the environment.

It is generally recognized that the skin should be protected with a moisturizer when the skin is dry. Products providing moisture to the skin as moisturizers are cosmetic products with a certain degree of elegance so that the user finds them pleasant to use usually as a cream or lotion and exhibits stability over the life of the product and is efficacious. The preferred moisturizing agents are mixtures of fats or lipids in the same major proportions as those commonly associated with the vernix.

The vernix is a naturally occurring mixture of lipid composed of specific lipids. The vernix lipid matrix can be processed from mammalian fetuses by commercially available chemical and mechanical processing equipment. The specific lipid mixture is composed of saturated fats at 1–1.5%, monounsaturated fats at 0.75–1.25%, polyunsaturated fats at 0.20–0.30%, phosphopids 4.0–4.5%, cephalin at 1.8–2.2%, sphenogomyelin at 2.25–2.75%, glycolipids at 2.25–2.75%, and aminopipids at 0.05–0.06%. The balance is keritens and other inert moities. A typical compositional analysis of the fatty acid components of the vernix which constitutes the active portion is as follows:

TABLE 1

| Fatty Acid Components of Human Vernix | Common Name | % by Wt Present |
|---|---|---|
| Total Saturated Fat | | 1.04 |
| C8 | Caprylic Acid | 0.005 |
| C10 | Capric Acid | 0.006 |
| C12 | Lauric Acid | 0.029 |
| C14 | Myristic Acid | 0.16 |
| C16 | Palmitic Acid | 0.59 |
| C18 | Stearic Acid | 0.17 |
| C20 | Arachidic Acid | 0.08 |
| Total Monounsaturated Fat | | 0.82 |
| C14:1 Cis | Myristoleic Acid | 0.011 |
| C14:2 Trans | Myristelaidic Acid | 0.010 |
| C16:1 Cis | Palmitoleic Acid | 0.065 |
| C16:1 Trans | Palmitolaidic Acid | 0.026 |
| C18:1 Cis | Oleic Acid | 0.28 |
| C18:1 Trans | Elaidic Acid | 0.23 |
| Total Polyunsaturated Fat | | 0.22 |
| C18:2 Cis | Linoleic Acid | 0.15 |
| C18:2 Trans | Linoelaidic Acid | 0.04 |
| C18:3 Cis | Linolenic Acid | 0.02 |
| C18:3 Trans | Elaidio-linolinic Acid | 0.006 |
| Total Phospholipid | | 4.27 |
| Cephalin | | 1.91 |
| Sphingomyelin | | 2.36 |
| Glycolipids | | 2.30 |
| Waxes | | 0.14 |
| Aminolipids | | 0.06 |
| Misc. Lipids | | 0.43 |
| % Total Lipid | | 9.28 |
| % Total Non Active | | 90.72 |
| Component (water, tissue, etc) | | 100.00% |

TABLE 2

| Fatty Acid Components only of Vernix Lipids | Common Name | % by Wt Present |
|---|---|---|
| Total Saturated Fat | | 11.21 |
| C8 | Caprylic Acid | 0.054 |
| C10 | Capric Acid | 0.065 |
| C12 | Lauric Acid | 0.313 |
| C14 | Myristic Acid | 1.724 |
| C16 | Palmitic Acid | 6.358 |
| C18 | Stearic Acid | 1.832 |
| C20 | Arachidic Acid | 0.862 |
| Total Monounsaturated Fat | | 8.84 |
| C14:1 Cis | Myristoleic Acid | 0.119 |
| C14:1 Trans | Myristelaidic Acid | 0.108 |
| C16:1 Cis | Palmitoleic Acid | 0.700 |
| C16:1 Trans | Palmitolaidic Acid | 0.280 |
| C18:1 Cis | Oleic Acid | 3.017 |
| C18:1 Trans | Elaidic Acid | 2.478 |
| Total Polyunsaturated Fat | | 2.37 |
| C18:2 Cis | Linoleic Acid | 1.616 |
| C18:2 Trans | Linoelaidic Acid | 0.431 |
| C18:3 Cis | Linolenic Acid | 0.215 |
| C18:3 Trans | Elaidio-linolinic Acid | 0.065 |

TABLE 2-continued

| Fatty Acid Components only of Vernix Lipids | Common Name | % by Wt Present |
|---|---|---|
| Total Phospholipid | | 46.01 |
| Cephalin | | 20.57 |
| Sphingomyelin | | 25.43 |
| Glycolipids | | 24.78 |
| Waxes | | 1.51 |
| Aminolipids | | 0.65 |
| Misc. Lipids | | 4.63 |
| % Total Lipid | | 100.00% |

The cosmetic preparations using the vernix lipids provide a method of treating dry and flaky skin conditions by topically applying those products to the affected skin areas.

The application of the above described vernix composition on the skin renders the skin soft and moist for prolonged time periods. Dried, chapped skin retains its elasticity in a favorable manner instantly. Upon incorporation into a cream or lotion a more elegant and desirable form for skin application is derived which has extraordinary moisturizing effects. Furthermore, it is hypoallergenic in use. Incorporation into skin products is easy and the active vernix retains its efficacy over prolonged time periods. The vernix is usually incorporated into sun screen products so that a moisturizing effect is obtained along with the sun screen effects.

DETAILED DESCRIPTION OF THE PRESENT INVENTION

The following examples represent suitable formulations incorporating the vernix composition in either its naturally occurring state or prepared by homogenizing the active components as described above from commercially available sources. These formulations represent formulations in which the formulated composition possesses specific efficacy based upon the synthesized vernix components or naturally occurring vernix. These formulations are biodegradable, hypoallergenic and bacteria free.

EXAMPLE 1

Moisturizing Lotion

| | % by Wt |
|---|---|
| Part A | |
| Vernix Lipids | 4.00 |
| Steareth-21 | 0.40 |
| Water | 82.00 |
| Part B | |
| Steareth-2 | 1.60 |
| Vernix Lipids | 10.50 |
| Dimethicone (100cs) | 1.50 |

Combine ingredients in both phases separately and heat to 65° C. Homogenize B into A with continued heating until mixed. Agitate, cool to 50° C. add fragrance, color and preservative as desired prior to filling.

EXAMPLE 2

Moisturizing Cream

| | % by Wt |
|---|---|
| Part A | |
| Water | 84.50 |
| Potassium hydroxide (45%) | 0.40 |
| Vernix Lipids | 4.10 |
| Part B | 0.50 |
| Titanium dioxide | |
| Part C | |
| Vernix Lipids | 9.50 |
| Dimethicone, 100cs | 0.50 |

Heat A with agitation to 60° C. Add B with mixing. Separately, heat C to 60° C. Homogenize C into A and B to obtain good emulsification. Stir cool to 45° C. Add fragrance and fill.

EXAMPLE 3

Massage Cream

| | % by Wt |
|---|---|
| Part A | |
| Vernix Lipids | 39.50 |
| Part B | 0.50 |
| CARBOMER 954 | |
| Part C | |
| Deionized water | qs to 100 |
| Part D | |
| Triethanolamine, 99% | 0.60 |
| Deionized water | 2.00 |
| Part E | |
| Maleated soybean oil | 2.00 |
| Part F | |
| Fragrance | 0.10 |
| Part G | |
| Propylene glycol | 7.00 |
| Methylparaben | 0.25 |
| Propylparaben | 0.25 |
| Part H | |
| Deionized water | 3.00 |
| Part J | |
| Cyclomethicone | 2.00 |

Heat A to 80° C., Mix B in C. Add premixed D to B and C mixture. Add A to B, C, D. Homogenize. Add E. Cool to 60° C. Add F. Cool to 45° C. Add premixed G, then H and J.

EXAMPLE 4

| BODY LOTION | % by Wt |
|---|---|
| Part A | |
| Vernix lipids | 5.00 |
| Titanium dioxide | 0.50 |

-continued

| BODY LOTION | % by Wt |
|---|---|
| Methylparaben | 0.30 |
| Water | 86.60 |
| Part B | |
| Steareth-2 | 1.80 |
| Cetyl alcohol | 1.20 |
| C12–15 alkyl benzoate | 1.50 |
| Isopropyl palmetate | 1.00 |
| Dimethicone | 2.00 |
| Propylparaben | 0.10 |

Heat A and B separately to 65°–70° C. Homogenize B into A. Stir cool to 45° C. and fill.

EXAMPLE 5

Moisturizing Water Resistant Sun Screen Gel

| | % by Wt |
|---|---|
| Part A | |
| Deionized water | qs to 100.00 |
| PVM/MA decadiene cross polymer (stabilized 06) | 0.40 |
| Part B | |
| Sodium hydroxymethylglycinate | 0.40 |
| Part C | |
| Phenoxyethanol | 0.60 |
| Part D | |
| Vernix lipids | 2.20 |
| Tocopherylacetate | 0.05 |
| Soluble collagen | 0.05 |
| Octyl methoxycinnamate or Octyl dimethyl PABA | 5.00 |
| Frangrance | 0.10 |

Heat A to 80°–85° C. and mix. Lower temperature to 60° C., add B. Mix. Add C then D, at one ingredient at a time in order listed. Mix well.

EXAMPLE 6

Lip Pomade

| | % by Wt |
|---|---|
| Part A | |
| Vernix lipids | 40.00 |
| Mineral oil | 12.00 |
| Ozokerite | 5.00 |
| Isopropyl myristate | 10.00 |
| Parafin wax | 7.00 |
| Part B | |
| Fragrance/Flavor | qs to 100 |

Melt A, mix until cool. Add B. Fill while still warm.

EXAMPLE 7

Sun Screen Lip Balm

| | % by Wt |
|---|---|
| Part A | |
| Vernix lipids | 42.50 |
| Octyl methoxycinnamate | 7.50 |
| Benzophenone 3 | 3.00 |
| Stearic acid | 15.00 |
| Cetyl alochol | 5.00 |
| Part B | |
| Acrylates/Octylpropenamide copolymer | 2.00 |
| Part C | |
| Carnauba wax | 5.00 |
| Candelillia wax | 20.00 |

Mix and heat A to 80° C. while slowly adding B. Mix until dissolved. Add C, mix at 80° C. until dissolved. Pour into molds.

EXAMPLE 8

Dry Skin Beauty Lotion

| | % by Wt |
|---|---|
| Part A | |
| Vernix lipids | 6.50 |
| C12–15 alkyl benzoate | 1.00 |
| Part B | |
| Methyl gluceth-20 benzoate | 5.00 |
| Triethanolamine (99%) | 0.80 |
| Distilled water | 86.40 |
| Methyl and propylparabens | 0.30 |

Heat A and B separately to 80° C. Add B to A with moderate agitation. Continue agitation while cooling to room temperature.

EXAMPLE 9

Thick Moisturizing Lotion

| | % by Wt |
|---|---|
| Part A | |
| Magnesium aluminum silicate | 0.15 |
| CARBOMER 980 | 0.15 |
| Part B | |
| Deionized water | 73.70 |
| Part C | |
| Propylene glycol | 5.00 |
| Part D | |
| Vernix lipids | 17.20 |
| Part E | |
| Preservative, fragrance Sodium hydroxide 10% sol'n to pH 6.0 | qs to 100 |

Blend A add slowly to B while stirring. Increase mixing speed and continue mixing. Add C. Mix D heat to 50° C., slow the mixing while cooling to 30° C. Add E, mix until uniform.

EXAMPLE 10

Aloe Vera Moisturizing Lotion

|  | % by Wt |
|---|---|
| Part A |  |
| Vernix lipids | 16.5 |
| Part B |  |
| Aloe Vera Gel | 80.0 |
| Glycerin 90% | 3.0 |
| Methyl and Propylparaben | 0.3 |
| Part C |  |
| Xanthangum | 0.2 |
| Fragrance and color | qs to 100 |

Heat Part A and B separately to 75° C. Add B to A slowly with mixing until homogeneous. Cool with mixing to 50° C. Add Part C. Continue cooling with mixing to 35° C. and fill.

EXAMPLE 11

Foot Cream

|  | % by Wt |
|---|---|
| Part A |  |
| Deionized water | 73.00 |
| Part B |  |
| Vernix lipids | 22.00 |
| Part C |  |
| Pumice | 4.00 |
| Part D |  |
| GERMABEN II | 1.00 |

Heat Part A to 70° C. Combine with Part B with mixing and heat to 80° C. Add Part C with mixing and cool to 40° C. Add Part D with mixing, cool and fill.

EXAMPLE 12

After Shave Moisturizer

|  | % by Wt |
|---|---|
| Part A |  |
| Vernix | 11.80 |
| Part B |  |
| Water | 54.35 |
| CARBOMER 934 | 0.40 |
| Part C |  |
| Water | 1.00 |
| Triethanolanmine 99% | 0.45 |
| Part D |  |
| Water | 20.00 |
| Thickener (CMC) | 3.50 |
| Part E |  |
| DOW CORNING 344 Fluid | 3.00 |
| SD Alcohol 40 | 5.00 |
| Preservative | 0.50 |

Heat A to 75° C. Combine B components with agitation until uniform-heat to 75° C. Add B to A under agitation. Mix components of C at 65° C. and add to B-A mixture. Add mixed D to existing combination at 55° C. At 45° C. add Part E mix until uniform.

EXAMPLE 13

Moisturizing Shampoo

|  | % by Wt |
|---|---|
| Part A |  |
| Water | 58.50 |
| Standapol A | 20.00 |
| Standapol ES-2 | 4.00 |
| Standamid LD | 3.00 |
| Monamid S | 0.50 |
| PEG - 150 Distearate | 0.50 |
| Tetrasodium EDTA | 0.10 |
| Citric Acid | 0.10 |
| Vernix | 10.00 |
| Panthenol | 0.10 |
| Cerasyn M | 0.50 |
| Part B |  |
| Perservative | 2.50 |
| Fragrance | 0.20 |

Mix Part A components at 80°–82° C. until uniform. Add Part B at 50° C. to homogenized A.

ADVANTAGES OF THE PRESENT INVENTION

Accordingly, the primary advantage of the present invention is that it provides various topically cosmetic preparations for the moisturization of human skin.

Another advantage of the present invention is it provides a physiological active agent capable of improving skin softness, flexibility, plasticity, elasticity and moisturization.

Another advantage of the present invention is it provides the user of a moisturizing active ingredient which comprises the material vernix.

Another advantage of the present invention is it provides the vernix as a naturally occurring material from mammalian fetuses or as a synthetically produced entity from commercially manufactured chemical compounds.

Another advantage of the present invention is it provides various cosmetic preparations in combination with vernix and other component materials which produces hypoallergenic, biodegradable and bacteria-free products.

Another advantage of the present invention is it provides cosmetic preparations in combination with vernix and component materials which produce products that have long lasting effects on the skin and results in longer effective treating times for any active ingredient which may be added.

It is still another advantage of the present invention that it provides such topical cosmetic preparations in the form of moisturizing lotions, moisturizing skin creams, massage creams, body lotions, face creams, skin healing ointments, sun screen gel, suntan lotions, lip pomades, sun screen lip balms, hand lotions, foot creams and hair lotions.

A still further advantage of the present invention is that it provides a method of treating dry and flaky skin conditions by topically applying the various cosmetic preparations as disclosed herein.

An even further advantage of this present invention is it provides such topical cosmetic preparations which substantially improves from a physiological standpoint, the condition of dry and flaky skin such that the treated skin areas provide a smooth, silky, velvety, long lasting feel after treatment.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Moreover, a latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A topically applied cosmetic preparation for moisturizing human skin comprising a dermatological acceptable carrier and a physiologically active ingredient, said active ingredient comprises lipids and the composition of said lipids approximates the composition of human vernix composition and has the following compositional ratio:

i) approximately one part saturated fatty acids;

ii) approximately one part monounsaturated fatty acids;

iii) approximately one quarter of a part polyunsaturated fatty acids;

iv) approximately four parts phosopholipids;

v) approximately two parts glycolipids; and vi) approximately two-thirds of a part of aminolipids, waxes and miscellaneous lipids.

2. The preparation according to claim 1 wherein the percent weight concentration of said physiologically active ingredient, per 100 parts by weight of composition, is between 2.2 to 42.5.

3. The preparation according to claim 1 wherein said matrix of specific lipids being fatty acids has the following composition:

| Fatty Acid Components | Common Name | % by Wt Present |
|---|---|---|
| Total Saturated Fat | | 11.21 |
| C8 | Caprylic Acid | 0.054 |
| C10 | Capric Acid | 0.065 |
| C12 | Lauric Acid | 0.313 |
| C14 | Myristic Acid | 1.724 |
| C16 | Palmitic Acid | 6.358 |
| C18 | Stearic Acid | 1.832 |
| C20 | Arachidic Acid | 0.862 |
| Total Monounsaturated Fat | | 8.84 |
| C14:1 Cis | Myristoleic Acid | 0.119 |
| C14:1 Trans | Myristelaidic Acid | 0.108 |
| C16:1 Cis | Palmitoleic Acid | 0.700 |
| C16:1 Trans | Palmitolaidic Acid | 0.280 |
| C18:1 Cis | Oleic Acid | 3.017 |
| C18:1 Trans | Elaidic Acid | 2.478 |
| Total Polyunsaturated Fat | | 2.37 |
| C18:2 Cis | Linoleic Acid | 1.616 |
| C18:2 Trans | Linoelaidic Acid | 0.431 |
| C18:3 Cis | Linolenic Acid | 0.215 |
| C18:3 Trans | Elaidio-linolinic Acid | 0.065 |
| Total Phospholipid | | 46.01 |
| Cephalin | | 20.57 |
| Sphingomyelin | | 25.43 |
| Glycolipids | | 24.78 |
| Waxes | | 1.51 |
| Aminolipids | | 0.65 |
| Misc. Lipids | | 4.63 |
| % Total Lipids | | 100.00% |

\* \* \* \* \*